United States Patent
Curtiss

(10) Patent No.: US 6,954,271 B2
(45) Date of Patent: Oct. 11, 2005

(54) SYSTEM AND METHOD FOR MULTIPLEXING INPUTS INTO A SINGLE SPECTROMETER

(75) Inventor: Brian Curtiss, Boulder, CO (US)

(73) Assignee: Analytical Spectral Devices, Inc., Boulder, CO (US)

( * ) Notice: Subject to any disclaimer, the term of this patent is extended or adjusted under 35 U.S.C. 154(b) by 134 days.

(21) Appl. No.: 09/974,094

(22) Filed: Oct. 10, 2001

(65) Prior Publication Data

US 2003/0067600 A1 Apr. 10, 2003

(51) Int. Cl.[7] .................................................. G01J 3/28
(52) U.S. Cl. ...................................... 356/328; 356/334
(58) Field of Search ................................ 356/326, 328, 356/319, 334, 445

(56) References Cited

U.S. PATENT DOCUMENTS

| | | | |
|---|---|---|---|
| 4,022,531 A | | 5/1977 | Orazio et al. |
| 4,259,014 A | * | 3/1981 | Talmi ..................... 356/328 |
| 4,375,919 A | | 3/1983 | Busch |
| 4,455,088 A | * | 6/1984 | Koike ..................... 356/334 |
| 4,494,872 A | * | 1/1985 | Busch ..................... 356/328 |
| 4,544,271 A | | 10/1985 | Yamamoto |
| 4,563,585 A | | 1/1986 | Ward |
| 4,875,773 A | | 10/1989 | Burns et al. |
| 4,966,458 A | * | 10/1990 | Burns et al. ............. 356/328 |
| 4,983,039 A | * | 1/1991 | Harada et al. ........... 356/328 |
| 5,066,127 A | * | 11/1991 | Schwenker ............... 356/328 |
| 5,251,007 A | * | 10/1993 | Rinke ..................... 356/319 |
| 5,283,624 A | * | 2/1994 | Tsukada et al. .......... 356/319 |
| 6,005,661 A | * | 12/1999 | Machler .................. 356/326 |
| 6,122,051 A | | 9/2000 | Ansley et al. |
| 6,184,985 B1 | | 2/2001 | Chalmers et al. |

FOREIGN PATENT DOCUMENTS

| | | |
|---|---|---|
| DE | 198 15 079 A1 | 10/1999 |
| FR | 2 822 235 A1 | 3/2001 |
| WO | WO 01/06232 A2 | 1/2001 |
| WO | WO 02/50783 A1 | 6/2002 |

OTHER PUBLICATIONS

Copy of the International Search Report for PCT Application Serial No. PCT/US02/32075, mailed on Feb. 12, 2003.
Spec Sheet for the FMX Series Fiber-Optic Multiplexer, Axiom Analytical, Inc.
Busch, Kenneth W. and Busch, Marianna A. (1990) "Multielement Detection Systems for Spectrochemical Analysis" John Wiley & Sons, New York, ISBN 0-471-81974-3; Chapter 5.

* cited by examiner

Primary Examiner—Layla G. Lauchman
(74) Attorney, Agent, or Firm—Cooley Godward LLP

(57) ABSTRACT

A spectrometer for measuring the intensity of light, comprises a grating having a major axis, a first entrance aperture aligned with the grating major axis and configured to direct light energy onto the grating, wherein the grating is adapted to produce a focused light beam, a first exit aperture aligned with the grating major axis and configured to accept the focused light beam, a second entrance aperture configured to direct the light energy onto the grating, wherein the second entrance aperture is offset from the grating major axis, and a second exit aperture configured to accept the focused light beam.

2 Claims, 12 Drawing Sheets

SYSTEM AND METHOD FOR MULTIPLEXING INPUTS INTO A SINGLE SPECTROMETER

FIELD OF THE INVENTION

The present invention pertains to spectrometer analysis and more particularly to the simultaneous measurement of several spectral properties using a single spectrometer.

BACKGROUND OF THE INVENTION

Optical spectrometers allow the study of a large variety of samples over a wide range of wavelengths. Materials can be studied in the solid, liquid, or gas phase either in a pure form or in mixtures. Various designs allow the study of spectra as a function of temperature, pressure, and external magnetic fields.

Grating spectrometers, in particular, make use of the diffraction of light from a regularly spaced ruled surface. They disperse the light by a combination of diffraction and interference rather than the refractive index variation with wavelength. The normal operation of a grating is the same as with a prism. The grating is rotated, and wavelength after wavelength passes a field stop and is detected by a sensor. In general, a grating spectrometer operates by focusing the light through an optical system to the field stop. In a classical spectrometer the field stop is a slit. This light is then collimated and passes through a transmission grating or passed to a reflective grating. The dispersed light is then either focused onto a spectral array or through an exit slit to a detector where it can be analyzed. While plane gratings require separate collimating optics, concave gratings combine the function of the grating and collimating optics into a single optical component.

Near-Infrared (NIR) spectroscopy is one of the most rapidly growing methodologies in pharmaceutical analysis. In particular, NIR is being increasingly used as an inspection method during the packaging process of pharmaceuticals, often augmenting or replacing previously used vision inspection systems. For example, an NIR inspection system can be used to inspect a blister packaging for, among other things, proper filling, physical aberrations, chemical composition, moisture content, and proper package arrangement.

The use of vision systems as an inspection mechanism is becoming less and less sufficient as the need for more in depth inspection procedures, and near 100% inspection processes, are desired and in many cases required. Of particular note is that vision systems are not capable of performing any sort of chemical analysis of the product being packaged, relying only on a comparison of a visual snapshot of the package to a reference image. A typical vision packaging inspection system "looks" at each individual package to see whether it has the correct number of doses in the pack, i.e. the system looks for missing or overfilled tablet wells. In some cases, physical discrepancies such as cracks or gouges on a tablet, will also cause a rejection of the package. The limitations of these types of vision systems become apparent when they are compared with the capabilities of a spectrometer adapted to function in a pharmaceutical packaging and inspection facility.

In high speed, large-volume processing, automated spectrometer-based monitoring systems have become indispensable in examining product flow in order to detect irregularities. Since these systems are meant in large part to replace vision systems, accuracy is a critical factor.

Known spectrometer designs typically incorporate a single entrance slit (field stop) and a single exit slit. The single exit slit typically corresponds to a single detector or other sensor and the measurement system requires a separate spectrometer (including entrance slit, exit slit, and grating) for each required simultaneous spectrum measurement. When multiple simultaneous spectrum measurements are desired, the cost and complexity of a spectrometer system capable of performing such analysis increases dramatically, particularly because of the need for multiple gratings. What is needed is a device and method that provides for multiple and simultaneous spectrum measurements while only requiring a single spectrometer.

SUMMARY OF THE INVENTION

In one aspect, a spectrometer having a reflective grating and the grating having a major axis, a light plate, comprises a plurality of entrance apertures, wherein at least one of the entrance apertures is offset from the grating major axis.

In another aspect, a spectrometer for measuring the intensity of light, comprises a grating having a major axis, a first entrance aperture aligned with the grating major axis and configured to direct light energy onto the grating, wherein the grating is adapted to produce a focused light beam, a first exit aperture aligned with the grating major axis and configured to accept the focused light beam, a second entrance aperture configured to direct the light energy onto the grating, wherein the second entrance aperture is offset from the grating major axis, and a second exit aperture configured to accept the focused light beam.

As will become apparent to those skilled in the art, numerous other embodiments and aspects will become evident hereinafter from the following descriptions and claims.

BRIEF DESCRIPTION OF THE DRAWINGS

The drawings illustrate both the design and utility of the preferred embodiments of the present invention, wherein.

DETAILED DESCRIPTION

Figure 1:
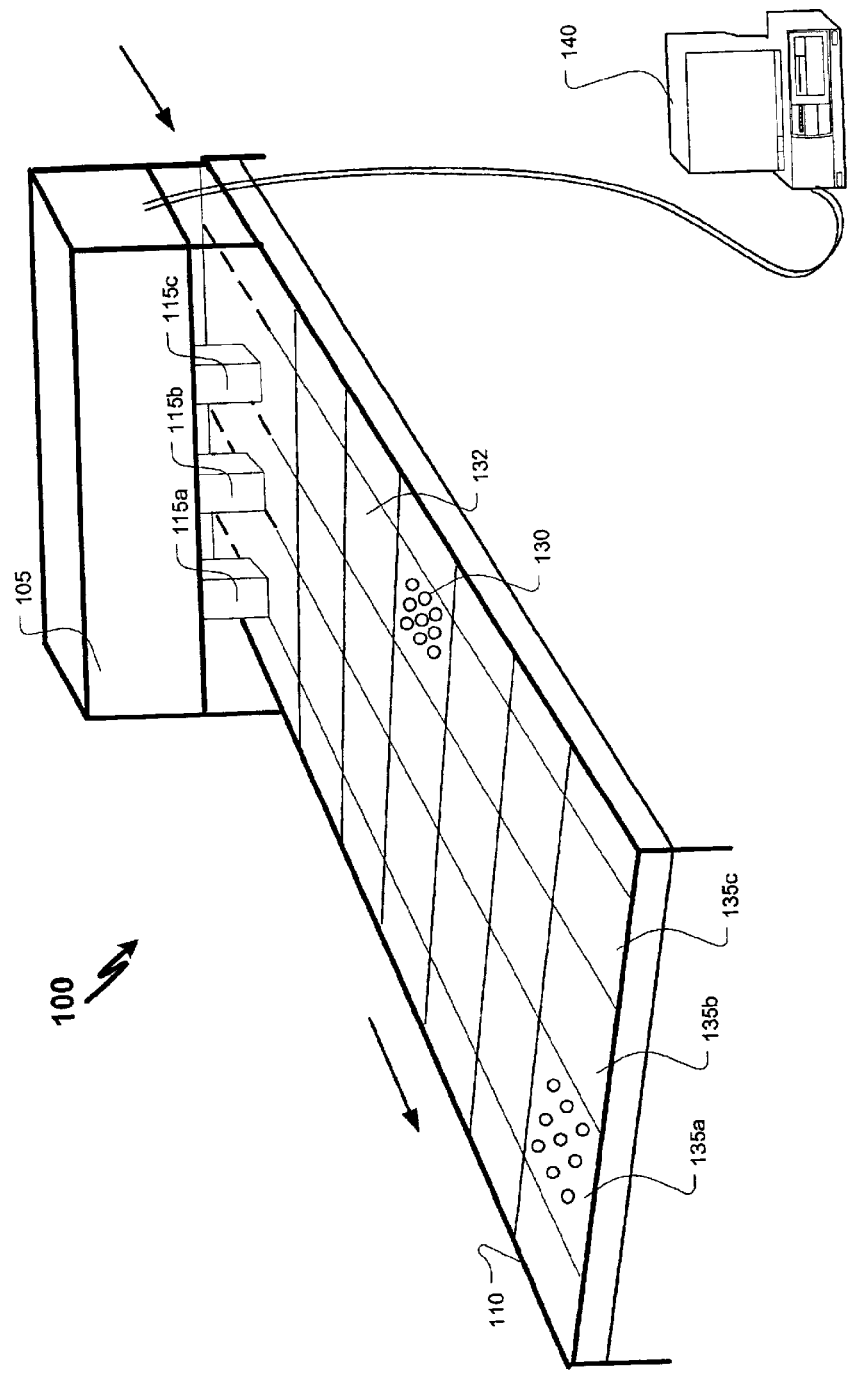
FIG. 1 shows a packaging line utilizing a spectrometer-based inspection system.

FIG. 1 shows a spectrometer-based tablet inspection system 100. The inspection system 100, generally includes a spectrometer head 105 mounted adjacent to or above a conveyer 110. The spectrometer head 105 has three individual sensors 115a, 115b, and 115c and is a substantially self-contained unit that includes a number of individual spectrometers, typically corresponding to the number of individual sensors. Therefore, in the example of FIG. 1, the spectrometer head 105 contains three spectrometers, one linked to each of the sensors 115a, 115b, and 115c. Depending on the application, a fewer or greater number of sensors/spectrometers can be incorporated into the inspection system 100. Generally, larger systems become more complex to operate and are more expensive, the individual spectrometers being the largest contributor to the cost and complexity of such an inspection system.

Positioned on the conveyer 110 is a pharmaceutical packaging unit 132 such as a blister pack, tablet well, ampul, or vial. As the packaging unit 132 passes the spectrometer head 105, it has already been filled with a product, such as a tablet or capsule 130, and is ready for inspection. The filling step typically occurs at a prior point in the manufacturing process. Typically, the packaging unit 132, filled with the tablets 130, are aligned in one or more rows 135a, 135b, and 135c. As positioned on the conveyer 110, each of the rows 135a, 135b, and 135c correspond to one of the sensors 115a, 115b, and 115c. The spectrometer head 105 is aligned so that each of the sensors 115a, 115b, and 115c are positioned substantially over a corresponding row 135a, 135b, or 135c. As the conveyer 110 moves each packaging unit 132 past the spectrometer head 105, a corresponding packaging unit 132 passes under one of the sensors 115a, 115b, and 115c. Readings taken by the sensors are fed to the spectrometer head 105 where information about the individual tablets 130 in the packaging unit 132 is analyzed. Defective or otherwise unacceptable packages/tablets are rejected at a subsequent stage in the manufacturing and packaging process. A computer 140 is linked to the spectrometer head 105 and is adapted to analyze the data gathered by the inspection system 100. Statistical information or other analytical data can be gathered by the computer 140 and sent to an operator for viewing or stored for later review and analysis.

Figure 2:
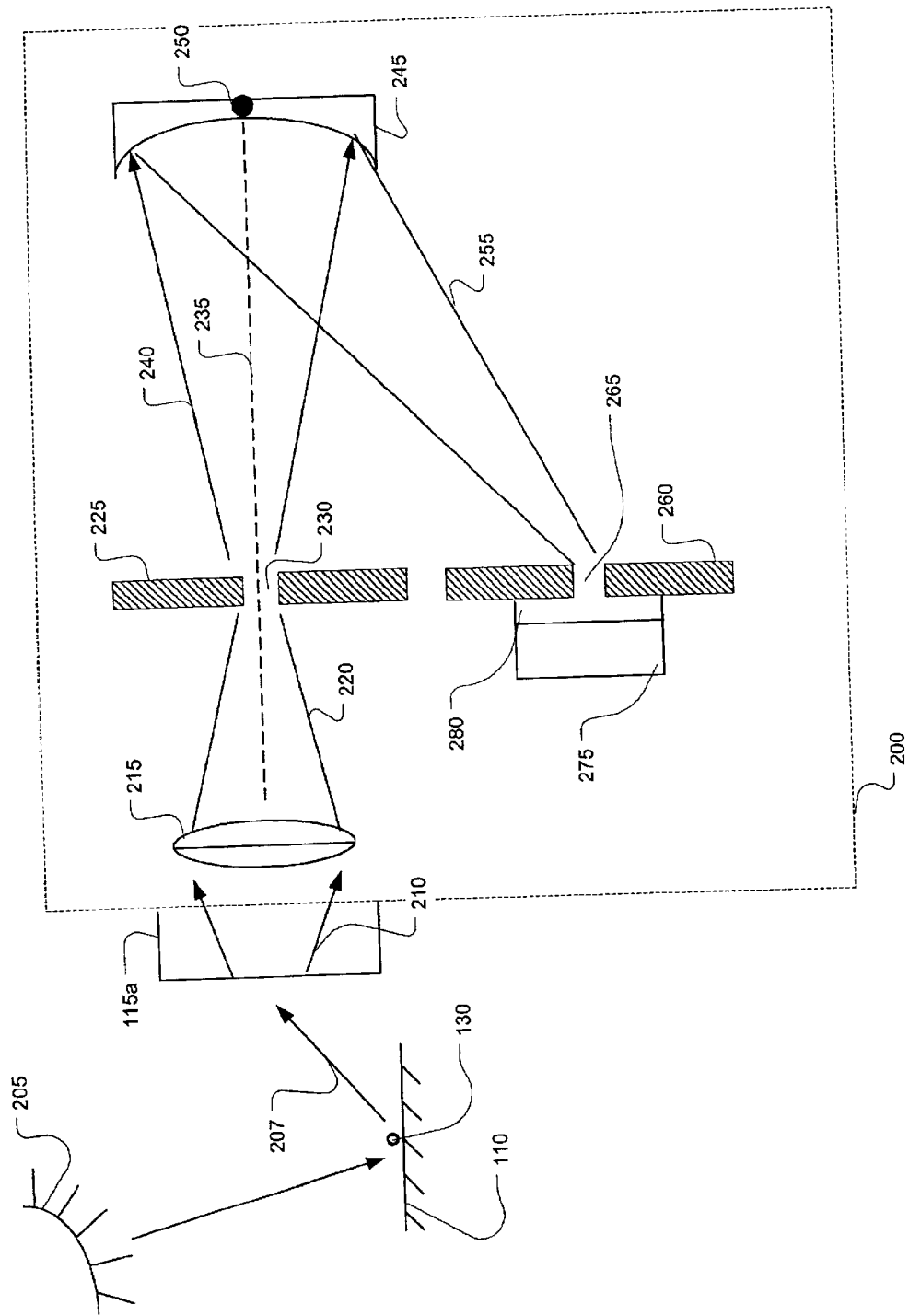
FIG. 2 is a diagrammatic representation of the spectrometer from FIG. 1.

In known systems, inspection systems are adapted so that each sensor is linked to a separate spectrometer and is therefore capable of only a single spectrum measurement at any given time, i.e. only one tablet can be inspected at a time by each sensor. A sensor must therefore take a separate reading for each tablet (or other product) contained within each packaging unit. FIG. 2 shows a diagrammatic representation of the single sensor 115a and its corresponding spectrometer 200.

A white light source 205 illuminates the tablet 130 passing on the conveyer 110 and generates reflected light energy 207. The reflected light energy 207 is collected by the sensor 115a and is passed into the spectrometer 200 as incoming light energy 210. In some applications, and as shown in FIG. 2, a lens 215 focuses the incoming light energy 210 into an outgoing beam 220 which is then directed at a light plate 225 containing an entrance slit 230. The light plate 225 and entrance slit 230 are aligned with a major axis 235 of a grating 245. In the example in FIG. 2, the grating 245 is a concave reflective scanning grating mounted on a pivot shaft 250. Since the grating 245 is mounted on a pivot shaft, it does not require separate collimating optics. Various other types and styles of gratings are also contemplated, such as transmissive gratings or a plane grating coupled with collimating optics. Light energy 240 is passed from the entrance slit 230 and directed at the grating 245. Light energy 255 that is reflected by the grating 245 is focused at a second light plate 260 that contains an exit slit 265. By rotating the grating 245 about the pivot shaft 250, different wavelengths of the light energy 240 are focused onto the exit slit 265. Mounted behind the exit slit 265 is a detector 275 that preferably includes a photo-cell 280 that is adapted to respond to the light energy 255. The detector 275 provides a measurement of the light energy 255 that corresponds to a specific physical property of the tablet 130. However, the measurement of different tablet properties cannot be achieved without moving sensor 115a and initiating another measurement. In these arrangements, simultaneous measurement of several tablet properties requires the addition of a separate sensor, spectrometer and grating for each simultaneous measurement desired.

It is generally understood that spectrometer designs incorporate a single entrance slit aligned with the major axis of the grating. This arrangement is referred to herein as an on-axis alignment and an on-axis entrance slit. Off-axis entrance slits, i.e. entrance slits that are not aligned with the major axis of the grating but are rather offset from the major axis, are known to result in the introduction of aberrations into the spectrum being measured. This degradation in performance is generally not acceptable for analytical measurements that require high precision and accuracy.

For those applications, however, where precision and accuracy of the raw spectrographic measurement is not a critical factor, the allowable tolerances of the spectral measurement allows for a certain amount of aberrations in the measured spectrum. For example, when accepting or rejecting a group of tablets based on the similarity of that group's spectrum as compared with the spectrum of known good tablets, such aberrations do not affect the performance of the system or the resulting measurements. Since this type of comparison is relative rather than absolute, the aberrations that perturb the spectrum do not influence the comparison as long as the perturbations are static. Known approaches to tablet inspection require that all spectra are measured with spectrometers having equivalent characteristics and therefore will not tolerate the introduction of these types of aberrations.

Figure 3:
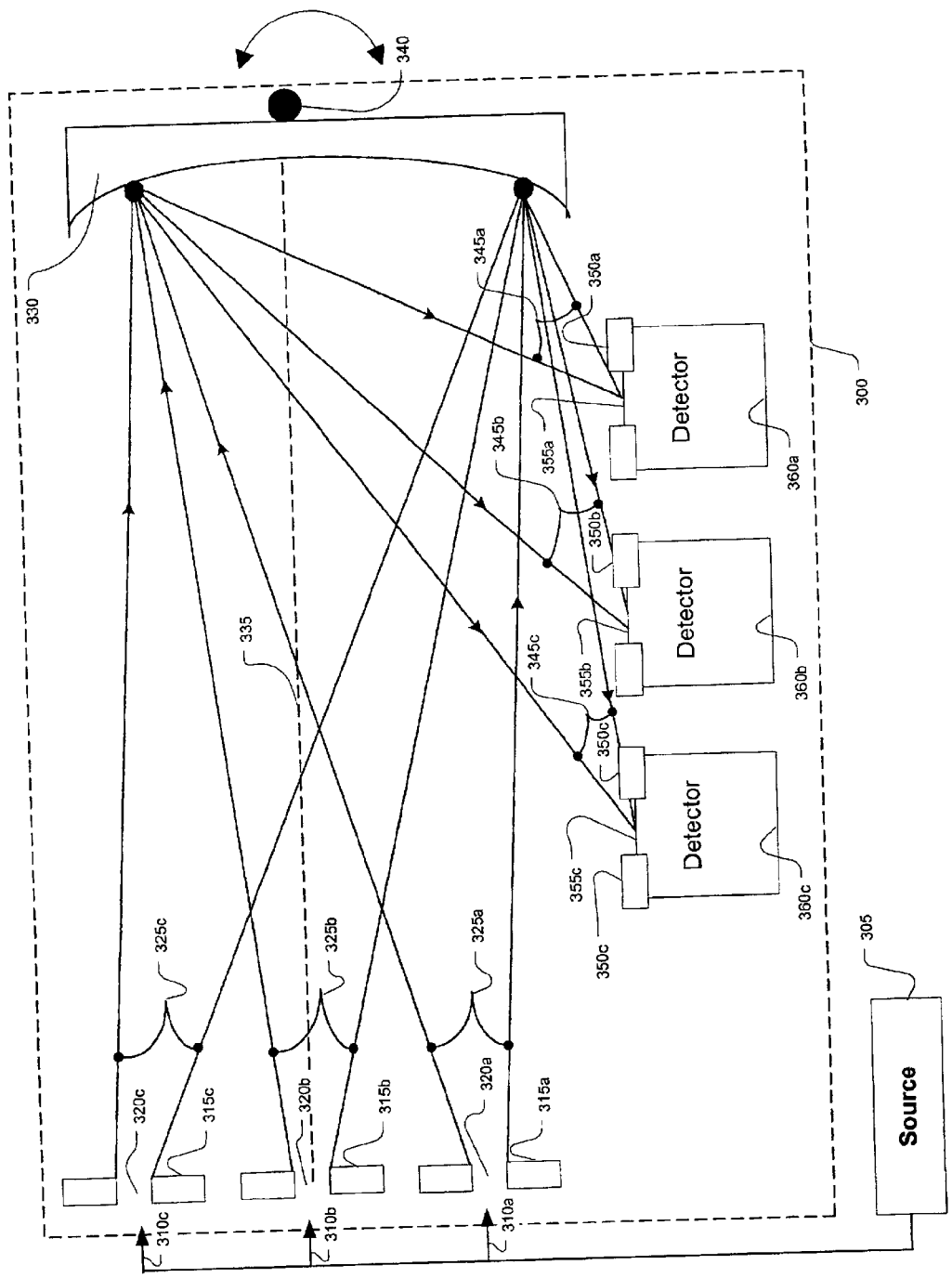
FIG. 3 is a diagrammatic representation of a multiplexed input spectrometer constructed in accordance with the present invention.

Referring to FIG. 3, a diagrammatic representation of a multiple input spectrometer 300 constructed in accordance with the present invention is shown. The diagram of FIG. 3 is meant only to be a diagrammatic representation of a multiple input spectrometer constructed in accordance with the present invention. For details of the physical layout of a multiple input spectrometer constructed in accordance with the present invention, reference should be made to FIGS. 3A and 4–11.

In FIG. 3, a source 305 delivers sampled light energy to the spectrometer 300 via a series of three inputs 310a, 310b, and 310c. The three inputs focus the light energy from the sample at three corresponding entrance light plates 315a, 315b, and 315c each of which includes an entrance slit (320a, 320b, and 320c respectfully). As shown in FIG. 3, the entrance light plate 315b and its corresponding entrance slit 320b are aligned with a major axis 335 of a grating 330, i.e. it is an on-axis entrance slit. The other two entrance light plates 315a and 315c, as well as the other two entrance slits 320a and 320c, are not aligned with the grating normal axis 335, rather, the entrance light plates 315a and 315c and the entrance slits 320a and 320c are offset from the grating normal axis 335 and are therefore referred to herein as "off-axis" entrance slits. Known spectrometers, the normal line to the grating and the exit slits all fall in the same plane. The normal to the grating is the line that is 90° to the plane defined by the front surface of the grating. In the case of a concave grating, the normal to the grating is a line that is 90° to a plane tangent to the center point (focus) of the grating.

After the sampled light energy passes through each of the entrance slits 320a, 320b, and 320c, it is directed as light rays 325a, 325b, and 325c onto the grating 330. The orientation and construction of the grating 330 determines which wavelength of the light is reflected and focused as light rays 345a, 345b, and 345c. The grating 330 as shown in FIG. 3 is a scanning grating and is thus mounted on a pivot shaft 340. The wavelength of the sampled light that is reflected as rays 345a, 345b, and 345c can thus be altered by rotating the grating through various angles. Each of the light rays described herein are in actuality individual rays of a cone of illumination and are shown as individual rays for ease of illustration and understanding.

Also positioned within the spectrometer 300 are a series of detectors 360a, 360b, and 360c. Each of the detectors 360a, 360b, and 360c is positioned adjacent an exit light plate (350a, 350b, and 350c respectively). Each of the exit light plates 350a, 350b, and 350c includes an exit slit 355a, 355b, and 355c. The reflected light rays 345a, 345b, and 345c are directed at each of the exit slits 355a, 355b, and 355c respectively. Detectors 360a, 360b, and 360c are positioned behind each of the exit slits. The detectors function to analyze the light energy that is passed through each of the respective exit slits 355a, 355b, and 355c. Alternately, each of the detector and exit slit pairs may be replaced with a detector array so that various wavelengths may be measured simultaneously without the need to rotate the grating.

The three entrance slit/exit slit/detector arrangement of the multiplexed spectrometer 300 can be utilized to analyze three different light energy samples simultaneously (by having three separate inputs to the entrance light plates/entrance slits). Increased throughput in an inspection systems utilizing such an arrangement is thereby realized because three tablets can be inspected simultaneously by a single spectrometer. Since the location of the off-axis entrance slits 320a and 320c are static, so are the aberrations that are reflected in the spectrum results from the corresponding samples. Since the aberrations are static, the relative spectrum measurements are not influenced and the comparison is not affected.

Figure 3A:
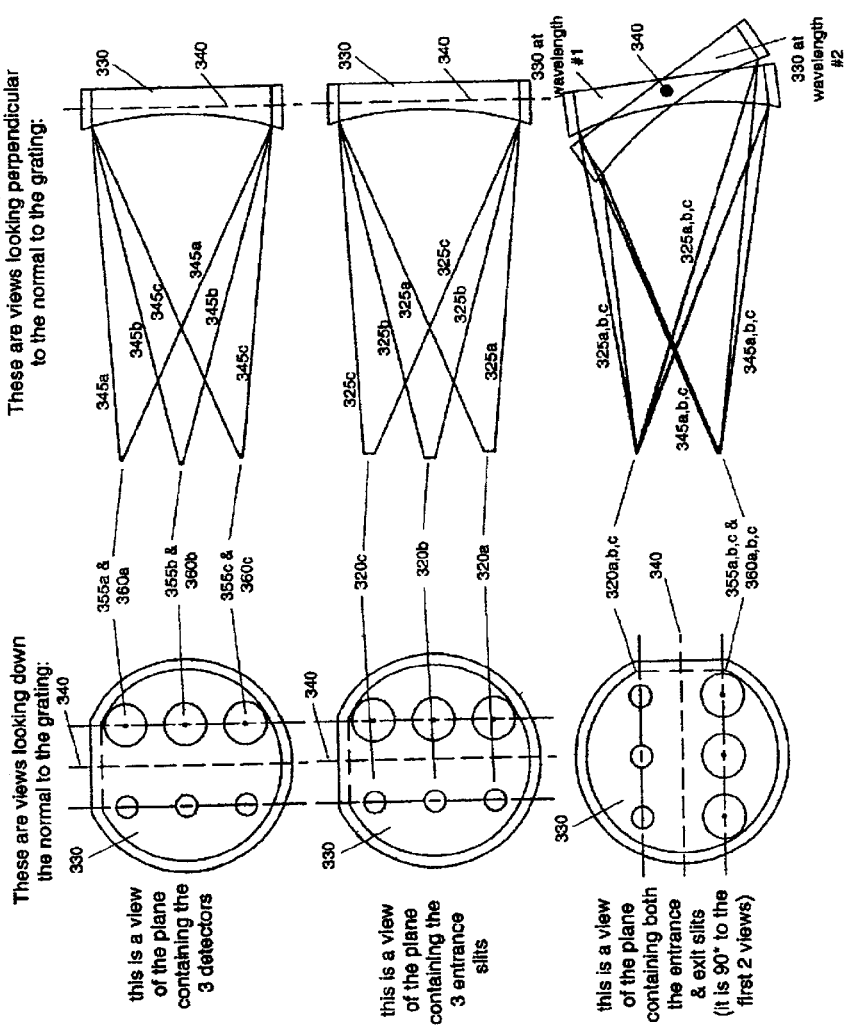
FIG. 3A is a physical representation of a multiplexed input spectrometer constructed in accordance with the present invention that corresponds to the diagram of FIG. 3.

FIG. 3A shows six views of a physical spectrometer constructed in accordance with the present invention that correspond to the diagrammatic representation of the spectrometer 300 from FIG. 3. The left column in FIG. 3A shows three views from behind the entrance and exit slits looking toward the grating and along the optical axis of the grating. The right column in FIG. 3A shows three views from the side of the spectrometer.

FIGS. 4–11 show various details of a preferred embodiment of a multiplexed input spectrometer constructed in accordance with the present invention. With attention to FIGS. 4 and 5, a light plate 400 and a reflective grating 440 are shown. The light plate 400 includes a set of three entrance slits 405, 410, and 415 and a set of three exit slits 455, 460, and 465. In alternate embodiments, the entrance slits and exit slits may be contained on separate light plates or a greater or fewer number of slits may be provided. Entrance slit 410 and exit slit 460 are on-axis since they are aligned with the major axis 435 of the grating 440. The remaining entrance and exit slits are off-axis since they are offset from the grating major axis 435.

Figure 4:
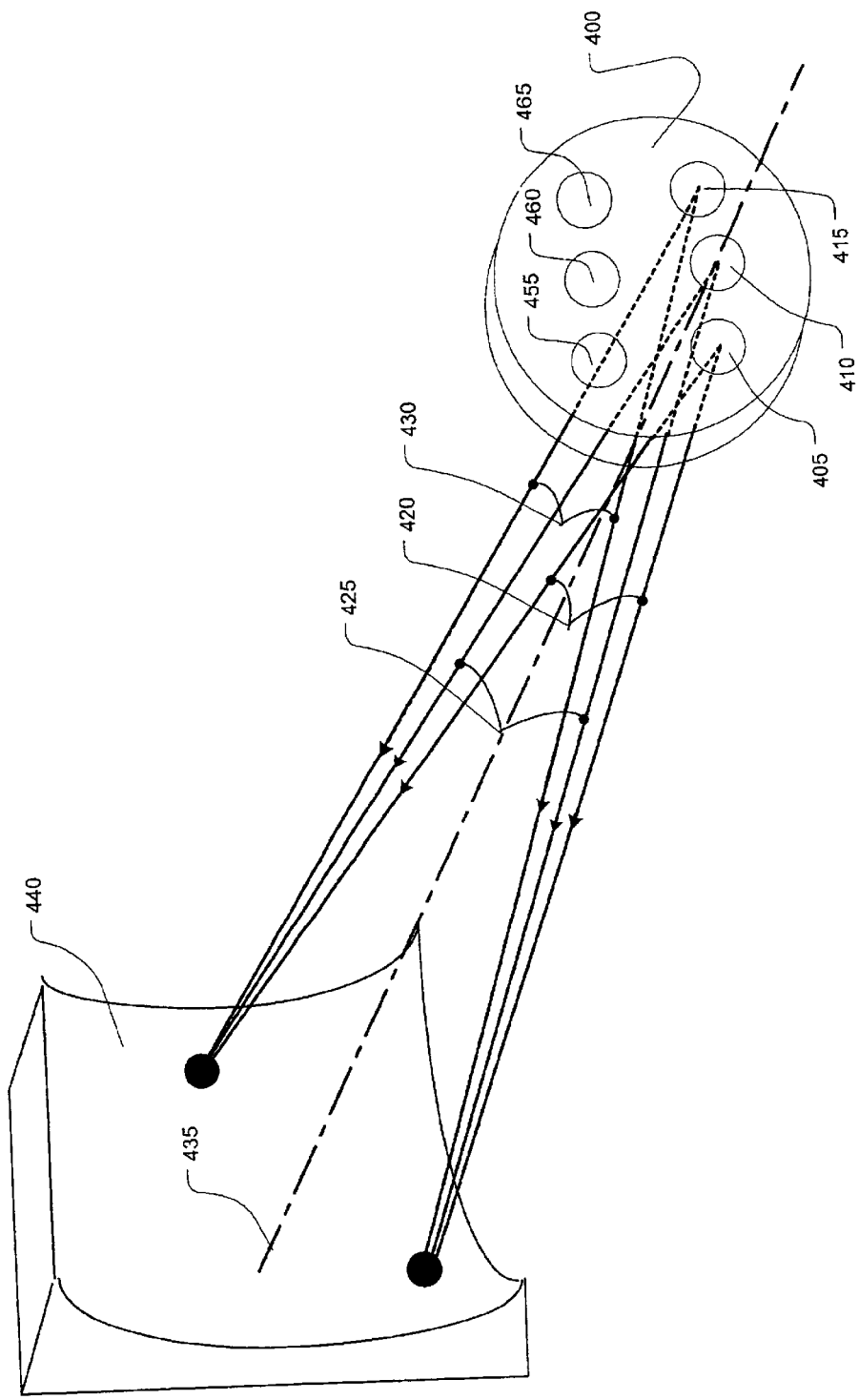
FIGS. 4–11 are details of a preferred embodiment of a multiplexed input spectrometer constructed in accordance with the present invention.

FIG. 4 shows how light energy is passed from the three entrance slits 405, 410, and 415 to the reflective grating 440. Line 435 depicts the major axis of the grating. The on-axis entrance slit 410 aligns with the major axis 435. Light entering the on-axis entrance slit 410 is passed to the reflective grating 440 in a cone of illumination. Light rays 425 are two such rays that comprise this cone of illumination. Light entering the off-axis entrance slit 405 is passed to the reflective grating 440 in a cone of illumination. Light rays 420 are two such rays that comprise this cone of illumination. Light entering the off-axis entrance slit 415 is passed to the reflective grating 440 in a cone of illumination. Light rays 430 are two such rays that comprise this cone of illumination.

Figure 5:
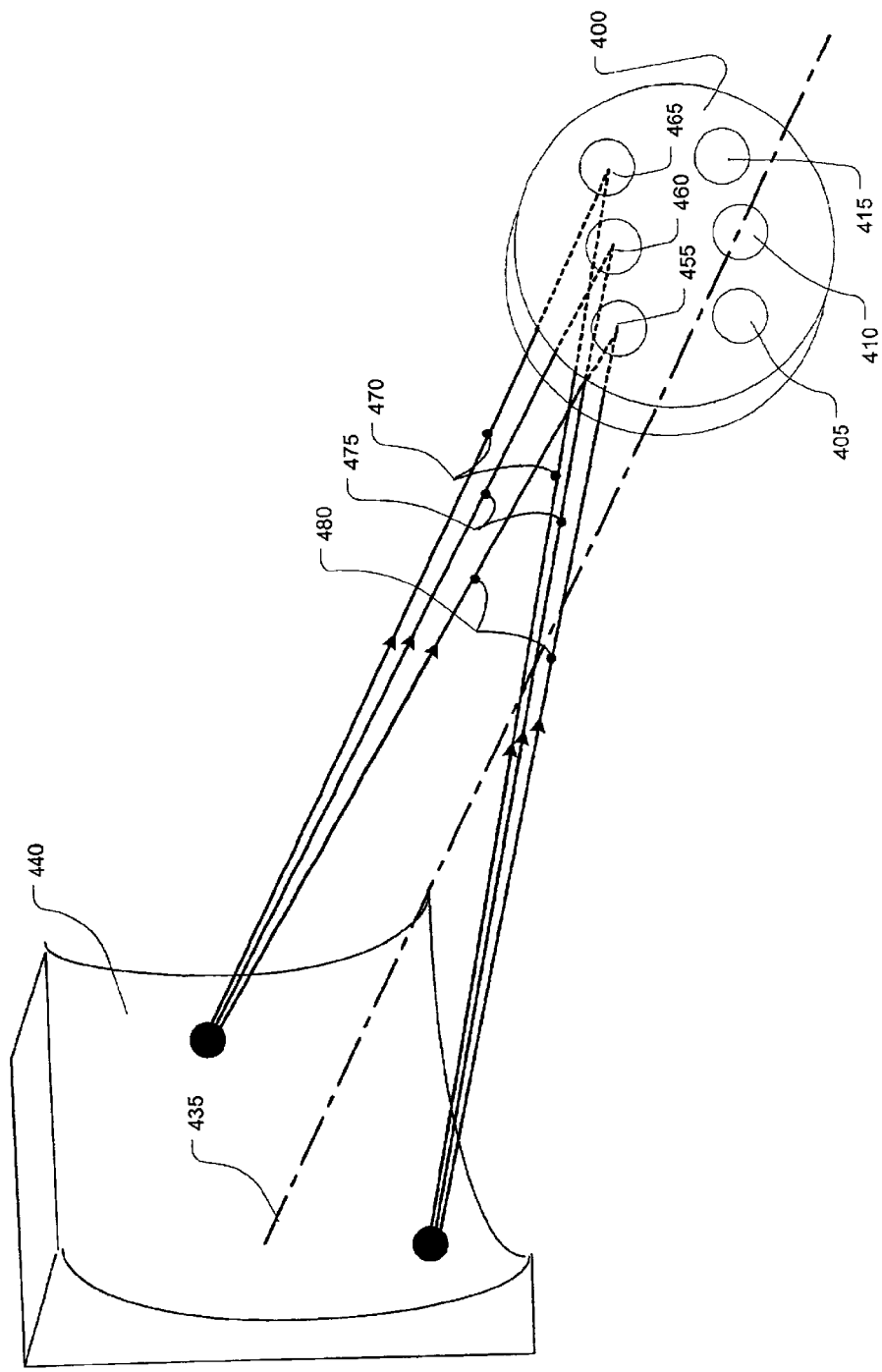

FIG. 5 shows how light energy is passed from the reflective grating 440 to the three exit slits 455, 460, and 465. The on-axis exit slit 460 aligns with the major axis 435. Light is passed from the reflective grating 440 to the on-axis exit slit 460 in a cone of illumination. Light rays 475 are two rays that comprise this cone of illumination. Light is passed from the reflective grating 440 to the off-axis exit slit 455 in a cone of illumination. Light rays 480 are two rays that comprise this cone of illumination. Light is passed from the reflective grating 440 to the off-axis exit slit 465 in a cone of illumination. Light rays 470 are two rays that comprise this cone of illumination.

Figure 6:
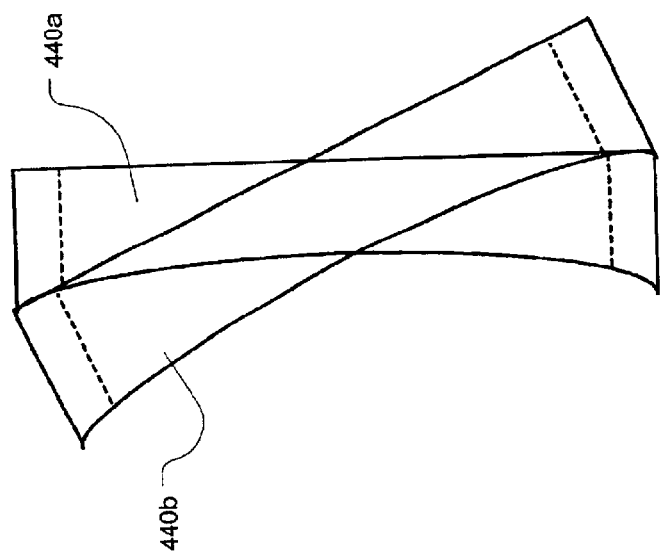
Figure 7:
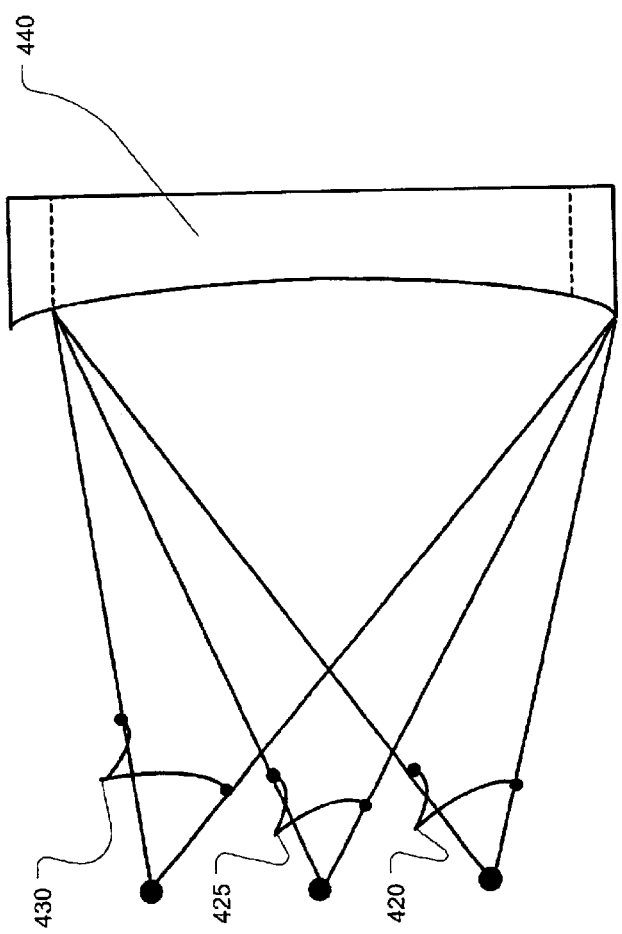
Figure 8:
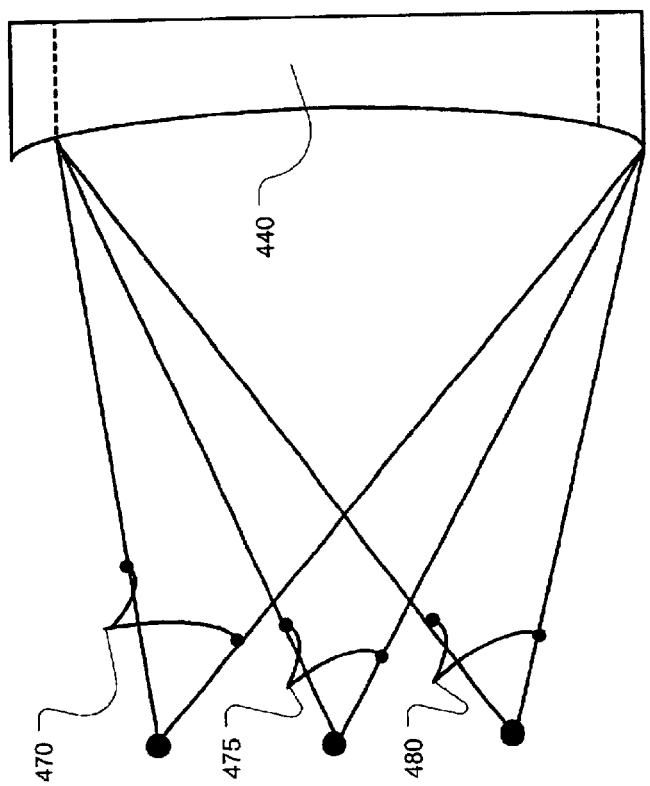
Figure 9:
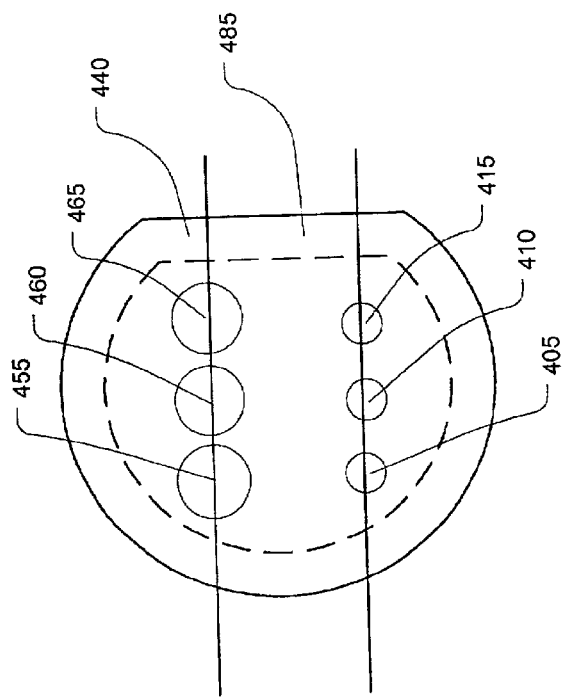
Figure 10:
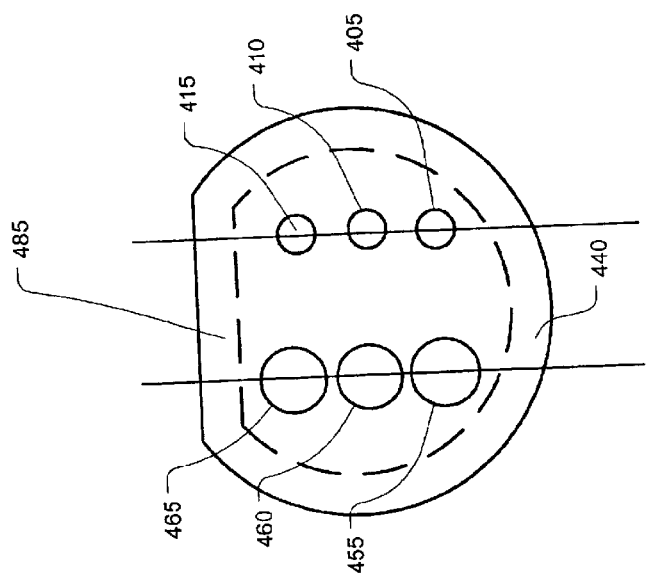
Figure 11:
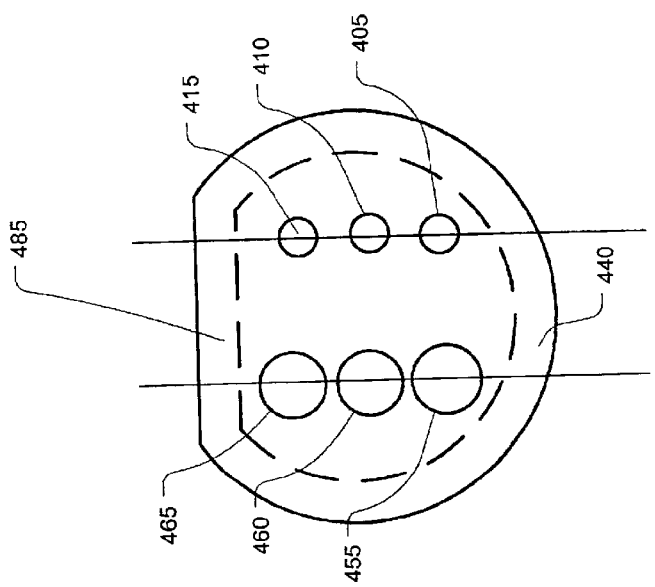

FIGS. 6–11 show various other views of the grating 440 and the manner in which light rays are passed from the entrance slits to the exit slits. FIG. 6 shows the grating 440 viewed perpendicular to the spectrometer's optical plane, including the grating at two different rotations, 440a and 440b. FIG. 7 shows the grating 440 viewed from within the spectrometer's optical plane while showing only the light rays 420, 425, and 430 from the entrance slits. FIG. 8 shows the grating 440 viewed from within the spectrometer's optical plane while showing only the light rays 470, 475, and 480 from the exit slits. Each of the light rays described herein are in actuality individual rays of a cone of illumination and are shown as individual rays for ease of illustration and understanding. FIGS. 9, 10, and 11 are the views perpendicular to the grating 440 that correspond respectively to FIGS. 6, 7, and 8. The flat edge 485 of the grating 440 is provided to ensure that the grating is properly oriented when installed in the spectrometer.

Although the present invention is particularly suited for use in connection with pharmaceutical capsules and tablets, it is to be clearly understood that the principals of this invention as well as the invention itself are applicable to and may be employed in connection with countless different types and kinds of solid discrete particular objects, including solid or multi-colored objects, liquids, powders, and various other substances.

Although the present invention has been described and illustrated in the above description and drawings, it is understood that this description is by example only and that numerous changes and modifications can be made by those skilled in the art without departing from the true spirit and scope of the invention. The invention, therefore, is not to be restricted, except by the following claims and their equivalents.

What is claimed is:

1. A multiple input spectrometer, comprising:

a grating having a surface and a major axis perpendicular to the surface; and a light plate, the light plate comprising a plurality of entrance slits, wherein at least one of the plurality of entrance slits is offset from the grating major axis, wherein the light plate further comprises a plurality of exit slits, wherein at least one of the plurality of exit slits is offset from the grating major axis.

2. The spectrometer of claim 1, further comprising:

means for directing a light source at the light plate; and means for simultaneously obtaining a spectra measurement through each of the plurality of exit slits.

* * * * *